United States Patent
Chen et al.

(10) Patent No.: US 6,974,832 B2
(45) Date of Patent: Dec. 13, 2005

(54) L-ASCORBIC ACID AND PECTIN COMPOSITION

(75) Inventors: Chyi-Cheng Chen, Binningen (CH); Bruno Leuenberger, Allschwil (CH); Denise Voelki, Zurich (CH)

(73) Assignee: DSM Nutritional Products Inc., Parsippany, NJ (US)

( * ) Notice: Subject to any disclaimer, the term of this patent is extended or adjusted under 35 U.S.C. 154(b) by 48 days.

(21) Appl. No.: 09/738,610

(22) Filed: Dec. 15, 2000

(65) Prior Publication Data

US 2001/0005514 A1 Jun. 28, 2001

(30) Foreign Application Priority Data

Dec. 22, 1999  (EP) ............................................. 99125639

(51) Int. Cl.[7] ........................ A61K 31/34; A61K 31/36; A61K 31/44
(52) U.S. Cl. ........................ 514/474; 514/464; 514/465; 514/474; 514/481
(58) Field of Search .................. 514/474, 464, 514/465, 481; 424/464, 465, 474, 481

(56) References Cited

U.S. PATENT DOCUMENTS

| | | | | |
|---|---|---|---|---|
| 3,312,594 | A | * | 4/1967 | Norman et al. ............. 424/117 |
| 3,459,863 | A | | 8/1969 | Apelian et al. ............. 424/280 |
| 3,490,742 | A | | 1/1970 | Nichols et al. ............... 252/99 |
| 3,615,591 | A | * | 10/1971 | Newlin et al. ................. 99/128 |
| 3,778,510 | A | | 12/1973 | Blonde ........................ 424/106 |
| 3,946,110 | A | * | 3/1976 | Hill ............................ 424/230 |
| 4,225,628 | A | * | 9/1980 | Lynn .......................... 426/549 |
| 4,372,968 | A | | 2/1983 | Kitamori et al. |
| 4,533,674 | A | | 8/1985 | Schmidt et al. ............. 514/474 |
| 4,605,666 | A | * | 8/1986 | Schmidt et al. ............. 514/474 |
| 5,008,254 | A | * | 4/1991 | Weibel ........................ 514/57 |
| 6,060,078 | A | | 5/2000 | Lee ............................ 424/440 |
| 6,123,963 | A | * | 9/2000 | Kim et al. ................... 424/482 |
| 6,136,347 | A | * | 10/2000 | Pollinger et al. ........... 424/495 |
| 6,217,903 | B1 | * | 4/2001 | Skinner ...................... 424/468 |
| 6,440,464 | B1 | * | 8/2002 | Hsia et al. .................. 424/725 |

FOREIGN PATENT DOCUMENTS

| | | |
|---|---|---|
| EP | 0 089 056 A2 | 9/1983 |
| EP | 0 875 245 A2 | 11/1998 |
| FR | 2 036 890 | 12/1970 |
| GB | 1109186 | 4/1968 |
| WO | WO 99/06029 | 2/1999 |

OTHER PUBLICATIONS

"Solaray Super Bio–Plex Vitamin C & Bioflavonoids", www.vitamins–etc.com, 1999.*
"GNC A–Z Chewable C 500mg with Cirturc C Complex, Fruit Flavor Tablets", Product Information Brochure, www.drugstore.com, 1999.*
Total C Product Information Brochure, www.nutripeak.com, 1998.*
"A Guide to Halal Food Selection", Hussaini et al., 1993.*
"Combined vacuum impregnation–osmotic dehydration in cryoprotection of apple", Chiralt et al., 1999, IFT Annual Meeting.*
Derwent English language abstract of EP 0 089 056 A2 (Document B3 above).
Derwent English language abstract of DE 19733094. a foreign counterpart to WO 99/06029 (Document B5 above).
Food Technology Dictionary, pp. 574–575, with attached English Translation of "fluidized bed dryer".
Ginter, E. et al., "*Natural Hypocholesterolemic Agent: Pectin plus Ascorbic Acid,*" Internat. J. Vit. Nutr. Res., vol. 49(4) pp. 406–412 (1979).
Vozár, J. et al., "*Effects of Pectin and Ascorbic Acid upon Glucose Tolerance and the Serum Lipid Levels,*" Vnitrni Lék., vol. 26(12) pp. 1183–1189 (1980).

* cited by examiner

Primary Examiner—Vickie Kim
Assistant Examiner—Brian S Kwon
(74) Attorney, Agent, or Firm—Bryan Cave LLP

(57) ABSTRACT

The invention relates to compositions in the form of a powder or granules containing L-ascorbic acid and/or a pharmaceutically acceptable salt thereof, and pectin in a quantity within the range of about 0.1 to about 10% by weight.

20 Claims, No Drawings

L-ASCORBIC ACID AND PECTIN COMPOSITION

FIELD OF THE INVENTION

The present invention relates to a composition in the form of a powder and/or granules, which contains as a principal component L-ascorbic acid and/or a pharmaceutically acceptable salt thereof, in combination with pectin.

BACKGROUND OF THE INVENTION

Different methods have been suggested for producing L-ascorbic acid powder or granules, which are directly compressible into tablets. Today, hydroxypropylmethylcellulose (HPMC) and starch are considered standard binders for producing such powders and granules. For sugar-free and starch-free tablets, the powder or granules are generally produced with HPMC as a binder, although the color stability of such powders or granules, and tablets obtained therefrom, is not sufficient.

SUMMARY OF THE INVENTION

In one aspect, the present invention relates to a composition in the form of a powder or granules containing:

(a) L-ascorbic acid and/or a pharmaceutically acceptable salt thereof, (b) pectin in the range of about 0.1 to about 10% by weight, calculated based on the total weight of the composition thereof, and (c) optionally, adjuvants and excipients in the range of 0.1 to 10% by weight calculated based on the total weight of the composition.

In another embodiment, the present invention relates to a method of producing the composition of the present invention. In still another embodiment, the present invention relates to tablets obtained from the composition of the present invention.

In another embodiment, a powder or granule composition is provided. This composition includes L-ascorbic acid and/or a pharmaceutically acceptable salt thereof, and about 0.1 to about 10% by weight of pectin, calculated based on the total weight of the composition thereof.

Another embodiment is a compressed tablet formed from a powder or granule composition containing L-ascorbic acid and/or a pharmaceutically acceptable salt thereof, and about 0.1 to about 10% by weight of pectin, based on the total weight of the composition.

A further embodiment is a process for preparing a powder or granule composition. This process includes preparing an aqueous slurry containing L-ascorbic acid and/or a pharmaceutically acceptable salt thereof and about 0.1% to about 10% by weight of pectin; and spray drying the slurry to form the powder or granule.

Another embodiment is a process for preparing a powder or granule composition. This process includes forming a fluidized bed containing fluidized particles of L-ascorbic acid and/or a pharmaceutically acceptable salt thereof within a fluidized-bed drying device fitted with spray means, the fluidized bed being fluidized by air or an inert gas. The process further includes spraying an aqueous solution of pectin in the form of an atomized mist onto the fluidized particles to deposit the pectin onto the fluidized particles.

DETAILED DESCRIPTION OF THE INVENTION

It was now been found that a composition containing L-ascorbic acid and/or its salts in combination with pectin, may be obtained in the form of a powder or of granules with greatly improved color stability. Tablets made from such compositions have good taste, mechanical strength, and/or hardness, and in addition surprisingly have greatly improved color stability compared to prior art tablets made with HPMC and starch. In a composition according to the present invention, the pectin preferably is present in a range of about 0.1 to about 10% by weight, calculated on the total weight of the composition.

L-ascorbic acid is known in the art. Numerous pharmaceutically acceptable salts thereof are known. The preferred form of L-ascorbic acid is sodium ascorbate.

Pectin is a polysaccharide and is described, for example, in *Industrial Gums*, pg. 257ff (3 ed., Academic Press, Inc., 1993). Commercial pectins are generally produced from either citrus peel or apple pomace. Other possible sources are sugarbeet, sunflower, and mango. Preferred pectins to be used in the present invention are citrus pectins, which generally have lighter color than apple pectins and, thus, do not impart significant color to the granule product.

In the present compositions, pectin is preferably used in the range of about 0.1% to about 10% by weight, more preferably in about 0.5% to about 5% by weight, such as, for example from about 0.5% to about 2% by weight, calculated based on the total weight of the composition. In the present invention a composition consisting of 95–99% by weight of L-ascorbic acid and/or a pharmaceutically acceptable salt thereof and 5–1% by weight of pectin, the two components totaling 100% by weight, i.e. with no other components present, yield tablets of very good quality and excellent color stability.

Adjuvants may optionally be added to the present compositions. Suitable adjuvants are, for example, starch, HPMC, and polyols. Preferably no adjuvants are added.

The composition of this invention may be produced by any method known in the art for the production of powders or granules. Preferred methods include, for example, fluidized-bed granulation, high-shear granulation, extrusion, spray-drying, and wet granulation methods.

For obtaining the composition of the present invention by spray-drying it is convenient to prepare an aqueous slurry of all the components. The slurry preferably has a solid content of about 10 to 70% by weight, more preferably about 25 to 50% by weight. The slurry is then spray-dried in a manner known in the art.

For obtaining a composition of the present invention by fluidized-bed granulation, it is convenient to use a known fluidized-bed granulating apparatus, which utilizes a fluidized-bed drying device fitted with a spray means. Preferably the L-ascorbic acid and/or a pharmaceutically acceptable salt thereof form the fluidized bed, which is fluidized by air or an inert gas, e.g. nitrogen. The pectin, as well as optional adjuvants, are dissolved in an appropriate amount of water and sprayed in the form of an atomized mist onto the fluidized particles in such a manner that the granulating and drying operations are accomplished in a single step. The granulating process is continued until the desired amount of the pectin binder has been deposited onto the fluidized particles. The granules are sieved to remove the fractions of granules, which are either too large or too small. Preferably, the particle size of the granules is between 100 and 1000 micron, more preferably between 125 and 750 micron.

The composition thus obtained may be compressed into tablets with conventional tabletting methods and machinery. Optionally, the powder or the granules may further be mixed with a lubricant or a mixture of lubricants and then compressed into tablets. If additional lubricant is used, it is preferably stearic acid or the magnesium or calcium salt thereof, or glyceryl behenate 45 (Compritol 888 ATO), preferably in an amount of about 0.5 to 4% by weight, calculated based on the total weight of the composition. The composition may also be mixed with excipients. Examples of excipients are dextrinized sucrose (Di Pac sugar), microcrystalline cellulose, or starch.

A single tablet as obtained according to the present invention contains preferably 50 mg to 1500 mg, more preferably 500 mg to 1000 mg of L-ascorbic acid and/or a pharmaceutically acceptable salt thereof, corresponding to an appropriate daily dose of vitamin C.

The following examples are provided to further illustrate the process of the present invention. These examples are illustrative only and are not intended to limit the scope of the invention in any way.

EXAMPLES

Example 1

L-ascorbic acid crystals (2475 g, Roche Ascorbic Acid Fine Granular, F. Hoffmann-La Roche AG), were placed in a stainless container of a wet granulator (Ultra Power model from KitchenAid, Michigan, USA). Pectin (27.36 g, Pectin USP, Danisco Ingredients, Denmark) was dissolved in distilled water (350 g). The pectin solution (151.3 g) was added to the ascorbic acid crystals over a period of 10 minutes with mixing. After the addition of pectin solution, the resulting paste was mixed for another 10 minutes and pressed through a screen with 2 mm-openings to form noodle-like particles, which were dried in trays in a 45° C./25% relative humidity (RH) room for 4 hours. The dry particles were milled and sieved to give the particle size distribution as shown in Table 1A.

TABLE 1A

| Particle size, micron | % wt |
|---|---|
| >710 | 0.7 |
| >500 | 16.2 |
| >355 | 29.8 |
| >250 | 19.9 |
| >125 | 21.9 |
| <125 | 11.4 |
| Total | 100 |

The granules were mixed with other excipients as shown in the following Table 1B and compressed at 20 KN to give 786 mg tablets.

The hardness of the tablet was 88N.

TABLE 1B

| Component | Parts by weight |
|---|---|
| Granule Sample | 108.64 |
| Roche Ascorbic Acid 90% Granulation | 79.66 |
| White Di Pac sugar | 301.27 |
| Compritol 888 ATO | 10.43 |

To evaluate the color stability, the granules were dried at 45° C. to about 0.08% moisture content, sealed in aluminum bags and stored at ambient temperature. The Whiteness Index (CIE) of the granules was determined at various time intervals using a Hunterlab Ultrascan B256 (Hunter Associates Laboratory, Inc., Reston, Va., USA). For comparison, the reduction in whiteness index was obtained by subtracting the whiteness indices determined at various storage times from the initial whiteness index. Granules with poor color stability show high whiteness index reduction.

Color Stability: Whiteness Index reduction: 1.07 (after 1 month), 2.70 (after 2 months)

Example 2

Example 1 was repeated with the exception that Hydroxypropylmethylcellulose (HPMC)(Methocel E15LV, The Dow Chemical Co., Michigan, USA) was used in place of pectin. The granule particle size distribution was as given in Table 2.

TABLE 2

| Particle size, micron | % wt |
|---|---|
| >710 | 0.3 |
| >500 | 14.4 |
| >355 | 35.0 |
| >250 | 23.2 |
| >125 | 19.8 |
| <125 | 7.4 |
| Total | 100 |

Compressed at 20 KN compression force, the hardness of the tablet was 75 N.

The color stability was determined according to Example 1. Color Stability: Whiteness Index reduction: 8.49 (after 1 month temperature), 27.1 (after 2 months).

A comparison of the tablets obtained according to Example 1 with those obtained according to Example 2 shows that granules or powder made with pectin as binder are far superior to preparations made with HPMC with regard to tabletting compressibility and color stability.

Example 3

Sodium L-ascorbate (F. Hoffmann-La Roche AG, Switzerland) was used. A pectin solution was prepared by dissolving 27.3 g of pectin (Pectin USP, 8.4% moisture content, Danisco Ingredients, Denmark) in 1000 g of water. Sodium ascorbate powder was placed in a Glatt Fluidized-Bed granulator (Model Uniglatt, Switzerland) and sprayed with a fine mist of pectin solution. The granulation conditions were as follows:

L-Sodium ascorbate: 594 g

Pectin solution: 246.6 g

Pectin solution spraying rate: 6.7 g/minute

Inlet Air temperature: 80° C.

a) The granules leaving the apparatus had a moisture content of 0.19% by weight, calculated based on the granule weight. The granule particles were sieved to give the particle size distribution as shown in Table 3A

TABLE 3A

| Particle size, micron | % wt |
|---|---|
| >710 | 12.16 |
| >500 | 18.03 |
| >355 | 22.90 |
| >250 | 16.42 |
| >125 | 16.82 |
| <125 | 13.67 |
| Total | 100 | b) The granules (125–750 micron fraction) as obtained in Example 3 were mixed with the excipients as shown in Table 3B and compressed into tablets of 767 mg weight.

TABLE 3B

| Component | Parts by weight |
|---|---|
| Sample | 108.64 |
| Roche Ascorbic Acid 90% Granulation | 79.66 |
| White Di Pac sugar | 301.27 |
| Compritol 888 ATO | 10.43 |

The tablet hardness at various compression forces is as follows:

Hardness (Compression Force): 118 N (5 KN), 145 N (10 KN), 174 N (15 KN), 203 N (20 KN), 224 N (25 KN), 246 N (30 KN)

Example 4

Example 3 was repeated with the exception that Hydroxypropylmethyl-cellulose (HPMC)(Pharmacoat, Shin-Etsu Chemical Co., Ltd., Tokyo, Japan) was used in place of pectin.

The granulation conditions were as follows:

L-Sodium ascorbate: 594 g

HPMC solution: 246.6 g

HPMC solution spraying rate: 6.7 g/minute

Inlet Air temperature: 80° C.

The granule particles were sieved to give the particle size distribution as shown in Table 4

TABLE 4

| Particle size, micron | % wt |
|---|---|
| >710 | 0.2 |
| >500 | 1.5 |
| >355 | 5.2 |
| >250 | 17.5 |
| >125 | 58.9 |
| <125 | 11.1 |
| Total | 100 |

The granules (125–750 micron fraction) were mixed with the same excipients set forth in Table 3B, and compressed into tablets of 767 mg weight.

The tablet hardness at various compression forces is as follows:

Hardness (Compression Force): 95 N (5 KN), 132 N (10 KN), 151 N (15 KN), 179 N (20 KN), 177 N (25 KN), 200 N (30 KN).

A comparison of Example 3 with Example 4 shows that granules or powder made with pectin as binder are far superior to preparations made with HPMC with regard to tabletting compressibility.

The invention being thus described, it will be obvious that the same may be varied in many ways. Such variations are not to be regarded as a departure from the spirit and scope of the invention and all such modifications are intended to be included within the scope of the following claims.

What is claimed is:

1. A powder or granule composition consisting of:
   (a) L-ascorbic acid and/or a pharmaceutically acceptable salt thereof, and
   (b) a binder consisting of about 0.1 to about 10% by weight of pectin, calculated based on the total weight of the composition thereof.

2. A composition according to claim 1 wherein the pharmaceutically acceptable salt of L-ascorbic acid is sodium ascorbate.

3. A composition according to claim 1 wherein the pectin is a citrus pectin.

4. A composition according to claim 1 wherein the pectin is present in the composition at about 0.5% to about 5% by weight, calculated based on the total weight of the composition.

5. A composition according to claim 4 wherein the pectin is present in the composition at about 0.5% to about 2% by weight, calculated based on the total weight of the composition.

6. A composition according to claim 1 wherein the composition consists of 95–99% by weight of L-ascorbic acid and/or a pharmaceutically acceptable salt thereof and 1–5 % by weight of pectin.

7. A compressed tablet formed from a powder or granule composition consisting of:
   (a) L-ascorbic acid and/or a pharmaceutically acceptable salt thereof;
   (b) a binder consisting of about 0.1 to about 10% by weight of pectin, based on the total weight of the composition; and
   (c) a lubricant or mixture of lubricants.

8. A compressed tablet according to claim 7 wherein the lubricant or a mixture of lubricants are selected from the group consisting of stearic acid, a magnesium salt of stearic acid, a calcium salt of stearic acid, and glyceryl behenate 45.

9. A compressed tablet according to claim 7 wherein the lubricant or a mixture of lubricants is present in the tablet in an amount of about 0.5 to 4% by weight, calculated based on the total weight of the composition.

10. A powder or granule composition for making tablets consisting of:
    (a) L-ascorbic acid and/or a pharmaceutically acceptable salt thereof, and
    (b) about 0.1 to about 10% by weight of pectin binder calculated based on the total weight of the composition thereof, the composition having a compressibility superior to a composition comprising L-ascorbic acid and/or a pharmaceutically acceptable salt thereof and about 0.1 to about 10% by weight of a standard binder.

11. A powder or granule composition for making tablets consisting of:
    (a) L-ascorbic acid and/or a pharmaceutically acceptable salt thereof,
    (b) about 0.1 to about 10% by weight of pectin binder calculated based on the total weight of the composition thereof, and
    (c) about 0.1 to 10% by weight of an adjuvent and/or an excipients selected from the group consisting of dextrinized sucrose (Di Pac Sugar) microcrystalline cellulose, starch, and mixtures thereof calculated based on the total weight of the composition,
    the composition having a compressibility superior to a composition comprising L-ascorbic acid and/or a pharmaceutically acceptable salt thereof and about 0.1 to about 10% by weight of a standard binder.

12. A composition according to claim 10 wherein the pharmaceutically acceptable salt of L-ascorbic acid is sodium ascorbate.

13. A composition according to claim 10 wherein the pectin is a citrus pectin.

14. A composition according to claim 10 wherein the pectin is present in the composition at about 0.5% to about 5% by weight calculated based on the total weight of the composition.

15. A composition according to claim 14 wherein the pectin is present in the composition at about 0.5% to about 2% by weight calculated based on the total weight of the composition.

16. A composition according to claim 10 wherein the composition consists of 95–99% by weight of L-ascorbic acid and/or a pharmaceutically acceptable salt thereof and 1–5% by weight of pectin.

17. A compressed tablet formed from a powder or granule composition consisting of:
- (a) L-ascorbic acid and/or a pharmaceutically acceptable salt thereof, and
- (b) about 0.1 to about 10% by weight of pectin binder, based on the total weight of the composition, the composition having a compressibility superior to a composition comprising L-ascorbic acid and/or a pharmaceutically acceptable salt thereof and about 0.1 to about 10% by weight of a standard binder.

18. A compressed tablet formed from a powder or granule composition consisting of:
- (a) L-ascorbic acid and/or a pharmaceutically acceptable salt thereof,
- (b) about 0.1 to about 10% by weight of pectin binder based on the total weight at the composition.
- (c) a lubricant or a mixture of lubricants selected from the group consisting of stearic acid a magnesium salt of stearic acid, a calcium taft of stearic acid glyceryl behenate (Compritol 888 ATO) and mixtures thereof and
- (d) an excipient selected from the group consisting of dextrinized sucrose (Di Pac Sugar) microcrystalline cellulose, starch, and mixtures thereof, the composition having a compressibility superior to a composition comprising L-ascorbic acid and/or a pharmaceutically acceptable salt thereof and about 0.1 to about 10% by weight of a standard binder.

19. A compressed tablet according to claim 18 wherein the lubricant or a mixture of lubricants is present in the tablet in an amount of about 0.5 to 4% by weight, calculated based on the total weight of the composition.

20. A compressed tablet formed from a powder or granule composition consisting of:
- (a) L-ascorbic acid and/or a pharmaceutically acceptable salt thereof,
- (b) about 0.1 to about 10% by weight of pectin binder, based on the total weight of the composition, and
- (c) an excipient selected from the group consisting of dextrinized sucrose (Di Pac Sugar), microcrystalline cellulose, starch, and mixtures thereof, the composition having a compressibility superior to a composition comprising L-ascorbic acid and/or a pharmaceutically acceptable salt thereof and about 0.1 to about 10% by weight of a standard binder.

* * * * *